United States Patent [19]
Winter et al.

[11] Patent Number: 5,951,828
[45] Date of Patent: Sep. 14, 1999

[54] CONTINUOUS DISTILLATION OF THERMOLABILE MONOMERS

[75] Inventors: Manfred Winter, Dittelsheim-Hessloch; Jacques Dupuis, Ludwigshafen; Michael Kröner, Bergholz-Rehbrücke, all of Germany

[73] Assignee: BASF Aktiengesellschaft, Ludwigshafen, Germany

[21] Appl. No.: 08/816,729

[22] Filed: Mar. 14, 1997

[30] Foreign Application Priority Data

May 10, 1996 [DE] Germany .................. 196 18 855

[51] Int. Cl.⁶ .................. B01D 3/10; B01D 3/34; B01D 3/42; C07D 233/000
[52] U.S. Cl. .................. 203/1; 203/60; 203/91; 203/99; 203/DIG. 19; 564/216
[58] Field of Search .................. 203/91, 1, 99, 203/3, DIG. 19, 60; 159/DIG. 10; 564/216, 123, 197

[56] References Cited

U.S. PATENT DOCUMENTS

| | | | |
|---|---|---|---|
| 4,230,533 | 10/1980 | Giroux | 203/1 |
| 4,308,131 | 12/1981 | Bannon | 203/DIG. 19 |
| 4,348,259 | 9/1982 | Jensen | 203/DIG. 19 |
| 4,814,505 | 3/1989 | Kroener et al. | 564/216 |
| 4,990,222 | 2/1991 | Aigner et al. | 203/91 |

FOREIGN PATENT DOCUMENTS

| | | |
|---|---|---|
| 61-289069 | 12/1986 | Japan . |
| 05230155 | 9/1993 | Japan . |
| 5 70 371 | 8/1977 | U.S.S.R. . |

*Primary Examiner*—Viginia Manoharan
*Attorney, Agent, or Firm*—Oblon, Spivak, McClelland, Maier & Neustadt, P.C.

[57] ABSTRACT

In a process for the continuous distillation of thermolabile monomers under reduced pressure in the presence of formamide in a column,

- the thermolabile monomers are continuously fed in liquid form, separately from formamide, into the lower part of the column up to the middle of the column,
- Formamide is vaporized with a vaporizer at the bottom of the column and, together with constituents having higher boiling points than the thermolabile monomers, is discharged from the bottom of the column and replaced by addition of fresh formamide,
- the thermolabile monomers are taken off at a side offtake in the upper third of the column, with the distillation being controlled such that the monomers contain less than 5% by weight of formamide, and
- a product stream containing constituents which have a lower boiling point than the thermolabile monomers is taken off at the top of the column.

7 Claims, No Drawings

CONTINUOUS DISTILLATION OF THERMOLABILE MONOMERS

The present invention relates to a process for the continuous distillation of thermolabile monomers under reduced pressure in the presence of formamide in a column.

EP-A-0 231 901 discloses a process for purifying N-vinylformamide by fractionally distilling the N-vinylformamide. N-vinylformamide is a thermolabile monomer. It is fractionally distilled by the known method in the presence of formamide at a pressure of from 0.5 to 30 mbar in a column, with the distillation being controlled such that the distillate comprises N-vinylformamide and from 0.1 to 15% by weight of formamide. This distillation process enables the production of monomer qualities from which homopolymers of N-vinylformamide having very high molecular weights can be prepared. Although this process offers decisive advantages in terms of the monomer quality compared with the fractional distillation of N-vinylformamide in the absence of formamide, the N-vinylformamide thus produced still contains impurities in the ppm range. These impurities have not yet been identified but they interfere in the polymerization because they lead to a limitation of the molecular weights of polymers.

The distillation of thermolabile monomers frequently results in formation of dissociation products which accumulate during the distillation and have an adverse effect on the course of the distillation. In some cases, this can even result in blockage of the distillation column. On the other hand, low-boiling dissociation products of thermolabile monomers can be present as impurities in the distillate.

It is an object of the present invention to provide an improved process for the distillation of thermolabile monomers.

We have found that this object is achieved by a process for the continuous distillation of thermolabile monomers under reduced pressure in the presence of formamide in a column if the thermolabile monomers are continuously fed in liquid form, separately from formamide, into the lower part of the column up to the middle of the column, Formamide is vaporized by means of a vaporizer at the bottom of the column and, together with constituents having higher boiling points than the thermolabile monomers, is discharged from the bottom of the column and replaced by addition of fresh formamide, the thermolabile monomers are taken off at a side offtake in the upper third of the column, with the distillation being controlled such that the monomers contain less than 5% by weight of formamide, and a product stream containing constituents which have a lower boiling point than the thermolabile monomers is taken off at the top of the column.

For the purposes of the present invention, thermolabile monomers are monoethylenically unsaturated monomers which decompose on distillation. The distillation of thermolabile monomers frequently results in the formation of impurities which interfere, even in the ppm range, with the polymerization of the distilled monomers. Such monomers include, for example, N-vinylcarboxamides. They can, for example, have a cyclic structure such as N-vinylpyrrolidone or substituted N-vinylpyrrolidones or they have an open-chain structure as can be described, for example, by means of the following formula:

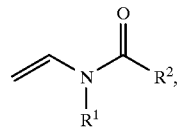

where $R^1$ and $R^2$ can be identical or different and are hydrogen or $C_1$–$C_6$-alkyl. Examples of monomers of this type are N-vinylformAmide ($R^1=R^2=H$ in formula I), N-vinyl-N-methylformamide, N-vinylacetamide, N-vinyl-N-methylacetamide, N-vinyl-N-ethylacetamide, N-vinyl-N-methylpropionamide and N-vinylpropionamide. The process of the present invention is particularly suitable for producing high-purity N-vinylformamide.

In the process of the present invention, the thermolabile monomers are continuously fed in liquid form, separately from formamide, into the lower part of the column up to the middle of the column. The monomers to be purified can contain both high-boiling and low-boiling constituents. Thus, for example, crude N-vinylformamide which can be prepared by pyrolysis of formylalanine nitrile and contains up to 40% by weight of formylalanine nitrile can be purified by the process of the present invention. The energy necessary for the thermal separation process within the column is introduced into the system by vaporization of formamide with the aid of a vaporizer at the bottom of the column. The temperature at the bottom of the column is, for example, from 70 to 140, preferably from 80 to 110° C. Constituents having higher boiling points than the thermolabile monomers accumulate at the bottom of the column. They are continuously discharged from the bottom of the column together with formamide and are continuously replaced by addition of fresh formamide. The formamide can be metered in gaseous or liquid form into the vaporizer or, if desired, in liquid form at a point up to the middle of the column. Preference is given to pumping liquid formamide into the vaporizer. The amount of formamide used is, for example, from 0.5 to 5 parts by weight, preferably from 1 to 3 parts by weight, based on 1 part by weight of the thermolabile monomers.

The thermal separation process within the column occurs as in a conventional distillation. The composition of the distillate depends essentially on the reflux ratio and on the number of theoretical plates in the column. The number of theoretical plates in the column is, for example, from 10 to 60, preferably from 25 to 40. The reflux ratio is, for example, set to a value in the range from 0.5:1 to 4:1. Adjustment of the reflux ratio enables, for example, the content of formamide in the distillate to be controlled easily.

The thermolabile monomers are taken from the column at a side offtake in the upper third of the column, with the distillation being controlled such that the monomers contain less than 5% by weight of formamide. Preferably, thermolabile monomers having a formamide content of less than 0.1% by weight are obtained at the side offtake of the column. Particular preference is given to an embodiment of the process of the present invention in which thermolabile monomers which are free of formamide are taken off at the side offtake. The temperature of the cooling water for the main condenser is set such that it is just sufficient to condense the thermolabile monomers while the lower-boiling impurities pass through the main condenser in gaseous form and are only condensed in the after-condenser. The difference between the temperature of the cooling water for the main condenser and the boiling point of the thermolabile monomer under the pressure conditions prevailing in the distillation is, for example, from 1 to 15, preferably from 2 to 12° C. Those constituents which are not condensed in the main condenser are taken off at the top of the column as a product stream containing compounds which have a lower boiling point than the thermolabile monomers. The product stream taken up at the top of the column is condensed in an after-condenser which is, for example, cooled with brine at from 0 to −20° C. The product stream separated off at the top of the column contains, for example, from 10 to 99.9% by weight, preferably from 85 to 98% by weight, of thermolabile monomers. The monomers separated off in this product stream are unsuitable for polymerization and have to be disposed of. The amount of product steam taken off at the top of the column is, for example, from 0.1 to 5% by weight, preferably from 0.2 to 2% by weight, based on the thermolabile monomers fed into the distillation.

Formamide is preferably vaporized in the bottom of the column. However, it can also be vaporized in a vaporizer outside the column and introduced into the column at a point between the column floor and the middle of the column. However, the thermolabile monomers are always fed into the column separately from formamide in liquid form above the metering-in point for the gaseous formamide. They can, if desired, be heated outside the column to a temperature up to about 5° C. below their boiling point under the distillation conditions.

Particular preference is given to purifying N-vinylformamide by the process of the present invention. The advantage of the process compared with known processes for fractionating N-vinylformamide is, in particular, that it gives monomer qualities which can be processed into particularly high molecular weight polymers. Thus, for example, N-vinylformamide distilled according to the present invention can be polymerized by the water-in-oil emulsion method to give poly-N-vinylformamide having Fikentscher K values above 240 (measured in a 5% strength by weight aqueous sodium chloride solution at 25° C., pH 7 and a polymer concentration of 0.1% by weight). The preparation of N-vinylformamide polymers having such a high molecular weight is difficult because even impurities present in a concentration of a few ppm have a considerable effect on the polymerization of N-vinylformamide.

In the process of the present invention, high-boiling by-products are discharged from the bottom of the column together with the condensed formamide and, possibly, small amounts of thermolabile monomers. The amounts of thermolabile monomers in the column bottoms are, for example, up to 2% by weight and are preferably in the range from 0 to 0.2% by weight. The formamide can be recovered from the column bottoms by means of fractional distillation and can be reused in the process of the present invention.

EXAMPLE 1

The column had a diameter of 200 mm and a length of 5000 mm. It contained stainless steel mesh packing having a surface area of 500 m$^2$/m$^3$. The packing in the column corresponded to about 25 theoretical plates. At the top of the column there was a main condenser which was operated using water at 50° C. The after-condenser at the top of the column was cooled with water at 5° C.

In the lower third of the column, 14 kg/h of crude N-vinylformamide which contained about 31% of formylalanine nitrile and had been preheated to 70° C. were introduced into the column. To provide heat input, 19 kg/h of gaseous formamide which had been heated to 100° C. were metered into the bottom of the column. The gaseous formamide was metered in such a way that the controlled temperature in the lower third of the column remained as constant as possible. The pressure at the top of the column was 3 mbar. A reflux ratio of 2:1 resulted in a main condensate, which was discharged at a side offtake in the upper third of the column, comprising 9.5 kg/h of N-vinylformamide having a purity of >99%. It contained 0.08% by weight of formamide.

Those materials which could not be condensed in the main condenser are condensed in the after-condenser and discharged separately. In steady-state operation, about 20 kg/h of product were obtained at the bottom of the column at a pressure of 12 mbar and 97° C. The bottom product contained <0.1% by weight of N-vinylformamide.

EXAMPLE 2

The continuous distillation was carried out using a column having a diameter of 40 mm and a length of 2000 mm. It contained stainless steel mesh packing having a surface area of 1000 m$^2$/m$^3$. The packing in the column corresponded to 40 theoretical plates. At the top of the column there was a main condenser which was operated using water at 40° C. The after-condenser at the top of the column was cooled with brine at 0° C. In the lower third of the column, 350 g/h of crude N-vinylformamide which had been preheated to 75° C. and contained 15% by weight of formylalanine nitrile was metered in. 100 g/h of liquid formamide were pumped to the vaporizer at the bottom of the column. The vaporizer power was regulated such that the temperature in the lower third of the column remained as constant as possible. The pressure at the top of the column was 2 mbar. 500 g/h of condensate were obtained in the main condenser and all of this was returned as runback to the column.

In the upper quarter of the column, 290 g/h of N-vinylformamide having a purity of more than 99% by weight were obtained as a liquid side stream. The proportion of formamide in this side stream was 0.08% by weight. Those materials which could not be condensed in the main condenser were condensed in the after-condenser and discharged. In steady-state operation, about 160 g/h of product were obtained at the bottom of the column at a pressure of 10 mbar (measured in the bottom of the column) at 95° C. The bottom product contained less than 0.1% by weight of N-vinylformamide.

EXAMPLE 3

The continuous distillation of N-vinyl-2-pyrrolidone was carried out using a column having a diameter of 40 mm and a length of 2000 mm. It contained stainless steel mesh packing having a surface area of 1000 m$^2$/m$^3$. The packing of the column corresponded to about 40 theoretical plates. At the top of the column there was a main condenser which was operated using water at 50° C. The after-condenser which was arranged above the main condenser was cooled using brine at 0° C. 300 g/h of N-vinylpyrrolidone which had been preheated to 75° C. were pumped continuously into the lower third of the column. 100 g/h of liquid formamide were continuously metered into the vaporizer at the top of the column. The vaporizer power was regulated such that the temperature in the lower third of the column remained as constant as possible. The pressure at the top of the column was 2 mbar. 600 g/h of condensate were obtained in the main condenser and all of this was returned as runback to the column. In the upper quarter of the column, 250 g/h of N-vinylpyrrolidone having a purity of more than 99% by weight and a formamide content of 0.06% by weight were obtained as a liquid side stream. Those materials which could not be condensed in the main condenser were condensed in the after-condenser and discharged separately. In steady-state operation, about 185 g/h of product were obtained at a pressure of 10 mbar (measured in the bottom of the column) and 95° C. The bottom product contained less than 0.1% by weight of N-vinylpyrrolidone.

We claim:

1. A process for continuous distillation of thermolabile monomers under reduced pressure in the presence of gaseous formamide in a column, comprising:

continuously feeding thermolabile monomers in liquid form, separately from formamide, above the metering-in point for the gaseous formamide, vaporizing formamide by means of a vaporizer at the bottom of the column and discharging formamide from the bottom of the column together with constituents having higher boiling points than the thermolabile monomers, adding fresh formamide, removing thermolabile monomers from a side off-take in the upper third of the column, while controlling the distillation such that said monomers contain less than 5% by weight of formamide, and taking a product stream containing constituents which have a lower boiling point than the thermolabile monomers off at the top of the column.

2. A process as claimed in claim 1, wherein the pressure at the top of the column during distillation is from 0.1 to 30 mbar.

3. A process as claimed in claim 1, wherein thermolabile monomers having a formamide content of less than 0.1% by weight are taken off at the side offtake of the column.

4. A process as claimed in claim 1, wherein thermolabile monomers which are free of formamide are taken off at the side offtake of the column.

5. A process as claimed in claim 1, wherein the thermolabile monomers used are N-vinylcarboxamides.

6. A process as claimed in claim 1, wherein the thermolabile monomer used is N-vinylformamide.

7. A process as claimed in claim 1, wherein the thermolabile monomer used is N-vinylpyrrolidone.

* * * * *